US00PP27369P3

(12) United States Plant Patent
Bradford et al.

(10) Patent No.: US PP27,369 P3
(45) Date of Patent: Nov. 15, 2016

(54) CHERRY TREE NAMED 'GLENCREST'

(50) Latin Name: *Prunus avium*
Varietal Denomination: Glencrest

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 107 days.

(21) Appl. No.: 14/544,248

(22) Filed: Dec. 15, 2014

(65) Prior Publication Data

US 2016/0174434 P1 Jun. 16, 2016

(51) Int. Cl.
*A01H 5/08* (2006.01)

(52) U.S. Cl.
USPC ..... Plt./181

(58) Field of Classification Search
USPC ..... Plt./181
See application file for complete search history.

(56) References Cited

U.S. PATENT DOCUMENTS

PP12,859 P2 8/2002 Bradford

*Primary Examiner* — June Hwu

(57) ABSTRACT

The present invention relates to a cherry tree, *Prunus avium*, and more particularly to a new and distinct variety broadly characterized by a medium size, moderately vigorous, hardy, self-unfruitful, productive and regular bearing tree. The fruit matures under the ecological conditions described in mid-May, with first picking on May 10, 2014. The fruit is uniformly medium in size, sweet in flavor, oblate in shape, fairly freestone in type, firm in texture, red in flesh color, very dark red in skin color, and it has a short but strongly attached stem. The variety is very useful to cross pollinate 'Glenred' (U.S. Plant Pat. No. 12,859).

1 Drawing Sheet

Botanical classification: *Prunus avium.*
Varietal denomination: 'GLENCREST'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of cherry tree, which has been denominated varietally as 'Glencrest'.

During a typical blooming season we isolate as seed parents individual cherry trees by covering them with screen houses. A hive of bees is placed inside each such house, and bouquets to provide pollen from different cherry trees are placed in buckets near the trees approximately every two days for the duration of the bloom. During 2002 one such house containing 'Glenred' (U.S. Plant Pat. No. 12,859) cherry tree was crossed by us in this manner. To pollinate this cherry, we selected bouquets from several sources of cherry trees without keeping specific written details. Upon reaching maturity the fruit from this cherry tree was harvested and the seeds were removed, cracked, stratified and germinated as a group with the label 'Glenred House'. They were grown as seedlings on their own root in our greenhouse, and upon reaching dormancy transplanted to a cultivated area of our experimental orchard located near Le Grand, Calif. in Merced County (San Joaquin Valley). During the summer of 2008 the claimed variety was selected by us as a single tree from the group of seedlings described above. Subsequent to origination of the present variety of cherry tree, we asexually reproduced it by budding and grafting in the experimental orchard described above, and such reproductions were true to the original tree in all respects. The reproduction of the variety included the use of 'Colt' (unpatented) rootstock, upon which the present variety was compatible and true to type.

The present variety is most similar to its seed parent, 'Glenred' (U.S. Plant Pat. No. 12,859) cherry, by being self-unfruitful, by having reniform glands, by being productive, and by producing fruit that is dark red in skin color, red in flesh color, oblate in shape, firm, sweet, and fairly crack resistant, but is distinguished therefrom by blooming about four days later, by possessing different s-alleles to make it useful as a cross pollinator, and by producing cherries that are somewhat smaller in size, that ripen about two days later, that are more heat tolerant, and that have a shorter stem that is more firmly attached to the fruit.

The present variety is also similar to 'Glenrock' (U.S. Plant Pat. No. 15,512) cherry, by being self-unfruitful, by having reniform glands, by blooming in mid March, by being productive, and by producing fruit that is dark red in skin color, partially red in flesh color, oblate in shape, firm, sweet, fairly freestone, and fairly crack resistant, but is distinguished therefrom by producing cherries that have a shorter stem and that ripen about ten day earlier.

SUMMARY OF VARIETY

In summary, the present cherry variety is characterized by a medium size, moderately vigorous, hardy, self-unfruitful, productive and regular bearing tree. The fruit matures under the ecological conditions described in mid-May, with first picking on May 10, 2014. The fruit is uniformly medium in size, sweet in flavor, oblate in shape, fairly freestone in type, firm in texture, red in flesh color, very dark red in skin color, and it has a short but strongly attached stem. The variety is very useful to cross pollinate 'Glenred' (U.S. Plant Pat. No. 12,859).

DRAWING

The accompanying photograph displays three whole fruits with the stems attached, four whole fruits detached from the stems to exhibit the skin color and form, two half fruits sectioned to reveal the flesh and fibers, an individual stone, two insets depicting flowers and buds, a typical tip shoot, and several leaves, all typical of the subject variety.

POMOLOGICAL CHARACTERISTICS

Referring now more specifically to the pomological characteristics of this new and distinct variety of cherry tree, the following has been observed under the ecological conditions prevailing near Le Grand, Merced County (San Joaquin Valley), Calif., and was developed at the state of firm ripe on May 14, 2014, on the original tree during its twelfth growing season. All major color code designations are by reference to the Inter-Society Color Council, National Bureau of Standards. Common color names are also used occasionally.

It is to be noted that 2014 was an abnormal year with drought conditions existing in California. The unusually clear, warm, and dry weather in January led to a very low amount of acquired chilling units, an earlier than normal blooming season, and an earlier than normal ripening season for the entire spring and summer.

PARENTAGE

Seed parent: 'Glenred' cherry (U.S. Plant Pat. No. 12,859).
Pollen parent: Unknown.

TREE

Size: Medium, maintained to a height of 11' [3.35 m.] and a spread of 7' [2.13 m.] after twelve growing seasons utilizing typical pruning.

Vigor: Medium vigor, responding typically to irrigation and fertilization. The plant should be grown on a standard commercial rootstock for production purposes.

Growth: Upright and medium dense.

Form: Central leader.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive.

Fertility: Self-sterile, must be cross pollinated by another early to mid seasonal blooming cherry variety, such as 'Glenred' (U.S. Plant Pat. No. 12,859). The present variety is also a very good cross-pollinator for 'Glenred'.

Bearing: Regular bearer, with no crop failures observed.

Trunk:

*Size*.—Medium, reaching a maximum diameter of 4½" [114.3 mm.] after the twelfth growing season.

*Texture*.—Medium smooth.

*Bark color*.—Grayish brown [61. gy.Br].

*Lenticels*.—Approximate Number Per Square Inch: 8. Color: Brownish Orange [54. brO]. Average Size: Length is ⅜" [9.5 mm.] with a width of 1/16" [1.6 mm.]. Shape: Eye-shaped, elongated.

Branches:

*Size*.—Diameter of main scaffold measured 12" above the first hanger is 3¼" [82.6 mm.].

*Texture*.—Smooth on first and second year wood, increasing roughness with age.

*Color*.—1st Year Wood topside: Light grayish red [18. l.gy.R]. 1st Year Wood underside: Brilliant yellow green [116. brill.YG]. 2nd Year Wood: Strong brown [55. s.Br]. 3rd Year and Older Wood: Moderate brown [58. m.Br].

*Lenticels*.—Number Per Square Inch: About 20 on second year wood. Color: Brownish orange [54. brO]. Average Size: Length is ⅛" [3.2 mm.] and width is 1/32" [0.8 mm.].

*Shape*.—Elongated.

Leaves:

*Size*.—Medium. Average Length: 5⅛" [130.2 mm.]. Average Width: 2⅜" [60.3 mm.].

*Arrangement*.—Alternate.

*Thickness*.—Medium.

*Form*.—Elliptical.

*Apex*.—Acuminate.

*Base*.—Acute to rounded.

*Surface*.—Smooth.

*Color*.—Dorsal Surface: Moderate olive green [125. m.OlG]. Ventral Surface: Moderate yellow green [120. m.YG].

*Margin*.—Finely serrate.

*Venation*.—Pinnately net veined.

*Vein color*.—Light yellow green [119. l.YG].

*Petiole*.—Average Length: 1⅜" [34.9 mm.]. Average Thickness: 1/16" [1.6 mm.]. Color: Grayish purplish pink [253. gy.pPk] on the topside, Strong yellow green [117. s.YG] underneath.

*Stipules*.—Number: 2 per leaf, up to 6 per growing tip. Average Length: ⅜" [9.5 mm.]. Color: Brilliant yellow green [116. brill.YG] toward the apex, Pale yellow green [121. p.YG] toward the base.

*Glands*.—Number: Usually 2 per leaf, occasionally 3. Position: Usually alternate, but a few are opposite. Size: Large. Form: Reniform or oval shaped. Color: Brilliant yellow green [116. brill.YG] with a Deep red [13. deep R] center.

*Leaf buds*.—Pointed, medium.

Flower buds:

*Hardiness*.—Hardy, with respect to central California winters.

*Diameter*.—Typically 5/16" [7.9 mm.] 3 days before bloom.

*Length*.—Typically ⅝" [15.9 mm.] 3 days before bloom.

*Form*.—Free, not touching.

*Surface*.—Non-pubescent.

*Tip color*.—White [263. White].

Flowers: Perfect, complete, perigynous, usually a single pistil, typically about twenty stamens, five sepals and petal locations alternately positioned.

*Average flower diameter*.—1½" [38.1 mm.].

*Average flower depth*.—½" [12.7 mm.] when fully open.

*Number of petals*.—Usually five, no extra petals or fragments observed.
*Petal arrangement*.—Overlapping.
*Petal shape*.—Circular to slightly oval.
*Petal margin*.—Somewhat wavy with a few notches present.
*Average petal diameter*.—11/16" [17.5 mm.].
*Average petal length*.—¾" [19.1 mm.].
*Petal apex*.—Rounded.
*Petal base*.—Rounded to slightly cuneate.
*Petal color*.—White [263. White] on both sides.
*Anther color*.—Light yellow [86. l.Y].
*Pollen*.—Anthers produce a moderate amount of Brilliant yellow [83. brill.Y] pollen.
*Stigma color*.—Light greenish yellow [101. l.gY].
*Stigma position*.—Typically located about even with the nearby anthers.
*Ovary*.—Non-pubescent.
*Sepal color*.—Moderate reddish orange [37. m.rO] over Light yellow green [119. l.YG] on the outer surface. The inner surface is Pale yellow green [121. p.YG].
*Sepal outer surface*.—Slightly pubescent.
*Sepal length*.—5/16" [7.9 mm.].
*Sepal width*.—3/16" [4.8 mm.].
*Sepal apex*.—Elliptical to match the sepal length and width.
*Sepal margin*.—Fairly smooth.
*Average pistil length*.—¾" [19.1 mm.].
*Average stamen length*.—⅝" [15.9 mm.].
*Pollen production*.—Moderate.
*Bloom density*.—Heavy.
*Blooming period*.—Early to medium, blooms four days after 'Glenred' (U.S. Plant Pat. No. 12,859).
*Onset of bloom*.—One percent on Mar. 12, 2014.
*Date of full bloom*.—Mar. 26, 2014.
*Duration of bloom*.—One to two weeks, dependent on ambient temperature.
*Number per cluster*.—Usually 2 to 8, 4 average.

FRUIT

Maturity when described: Firm ripe, May 14, 2014.
Date of first picking: May 10, 2014.
Date of last picking: May 18, 2014.
Size: Uniform, medium.
*Average diameter axially*.—1⅛" [28.6 mm.].
*Average diameter across cheek plane*.—1 5/16" [33.3 mm.].
*Average diameter across suture plane*.—⅞" [22.2 mm.].
*Typical weight*.—0.35 ounces [9.9 grams].
Form: Uniform, symmetrical, oblate.
*Axial view form*.—Elliptical.
*Suture plane form*.—Oval to round.
*Cheek plane form*.—Oblate.
Suture: A Blackish red [21. blackish R] line located in a shallow trough, extending from the stem cavity to just beyond the apex.
Ventral surface: Rounded, lipped slightly toward the apex on both sides.
Lips: Equal.
Cavity: Flaring, rounded, suture showing on one side.
*Depth*.—3/16" [4.8 mm.].
*Breadth*.—½" [12.7 mm.].
Base: Rounded, cordate if viewed parallel to the suture.
Apex: Rounded, to slightly cordate if viewed parallel to the suture.
Pistil point: A Grayish yellow [90. gy.Y] dot.
Stem: Short.
*Average length*.—1" [25.4 mm.].
*Average width*.—1/16" [1.6 mm.].
*Attachment*.—Very strong.
Skin:
*Thickness*.—Medium.
*Surface*.—Smooth.
*Tenacity*.—Tenacious to the flesh.
*Astringency*.—Slight.
*Tendency to crack*.—Rarely observed in dry seasons, fairly resistant to cracking in wet season.
*Color*.—Very deep red [17. v.d.R] smoothly blending to a Dark red [16. d.R] background.
Flesh:
*Color*.—Deep red [13. deep R] with Moderate yellowish pink [29. m.yPk] fibers throughout.
*Surface of pit cavity*.—Covered with Moderate red [15. m.R] fibers.
*Amygdalin*.—Moderate.
*Juice*.—Abundant, rich.
*Juice color*.—Deep red [13. deep R].
*Texture*.—Firm, crisp, melting.
*Fibers*.—Abundant, fine, tender.
*Ripens*.—Mostly even, slightly earlier on the shoulders.
*Flavor*.—A nice balance of acid and sugar, typically 18 to 20 brix.
*Aroma*.—Very slight.
*Eating quality*.—Very good.

STONE

Type: Fairly freestone.
Form: Oval.
Hilum: Narrow, oblong.
Base: Oblique.
Apex: Acute.
Sides: Equal.
Surface: Fairly smooth.
External color of stone: Light yellowish brown [76. l.yBr].
Pit wall color when cracked: Pale orange yellow [73. p.OY].
Cavity surface color: Dark orange yellow [72. d.OY].
Average pit wall thickness: 1/16" [1.6 mm.]
Average width: ⅜" [9.5 mm.].
Average length: 7/16" [11.1 mm.].
Average breadth: 5/16" [7.9 mm.].
Tendency to split: None observed.
Kernel:
*Form*.—Oval.
*Skin color*.—Pale yellow [89. p.Y] when first removed.
*Pellicle color*.—Yellowish gray [93. yGy].
*Vein color*.—Grayish yellow [90. gy.Y].
*Taste*.—Bitter.
*Viable*.—Yes.
*Average width*.—7/32" [5.6 mm.].
*Average length*.—5/16" [7.9 mm.].
*Amygdalin*.—Moderate.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of cherry tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of cherry tree, substantially as illustrated and described, that is most similar to its seed parent, 'Glenred' (U.S. Plant Pat. No. 12,859) cherry, by being self-unfruitful, by having reniform glands, by being productive, and by producing fruit that is dark red in skin color, red in flesh color, oblate in shape, firm, sweet, and fairly crack resistant, but is distinguished therefrom by blooming about four days later, by possessing different s-alleles to make it useful as a cross pollinator, and by producing cherries that are somewhat smaller in size, that ripen about two days later, that are more heat tolerant, and that have a shorter stem that is more firmly attached to the fruit.

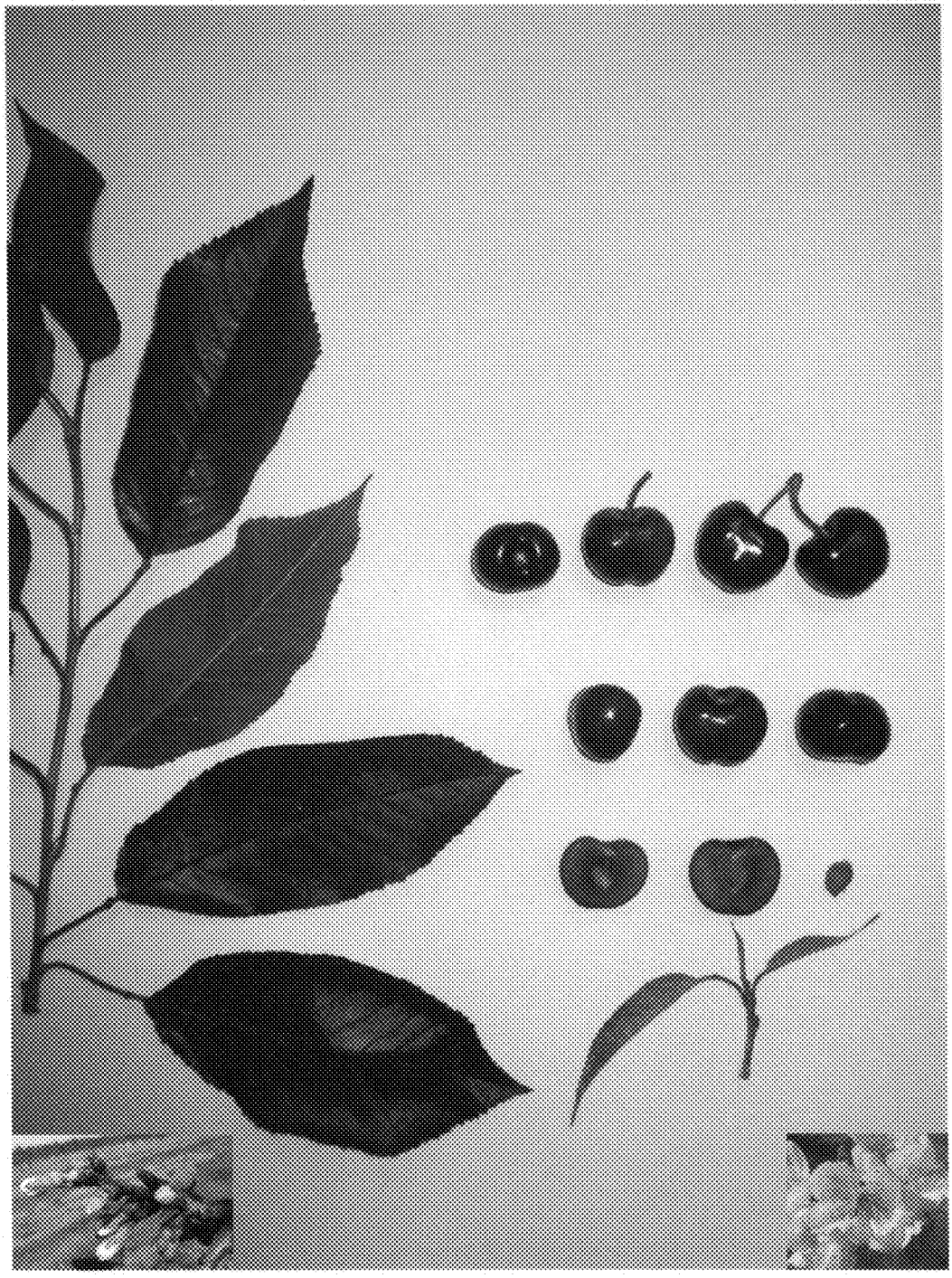

* * * * *